United States Patent [19]
Tu et al.

[11] Patent Number: 5,876,340
[45] Date of Patent: Mar. 2, 1999

[54] ABLATION APPARATUS WITH ULTRASONIC IMAGING CAPABILITIES

[75] Inventors: Hosheng Tu, Tustin; Weng-Kwen Raymond Chia, Irvine, both of Calif.

[73] Assignee: Irvine Biomedical, Inc., Irvine, Calif.

[21] Appl. No.: 840,905

[22] Filed: Apr. 17, 1997

[51] Int. Cl.⁶ .............................. A61B 8/00; A61B 17/39
[52] U.S. Cl. .................... 600/439; 600/381; 600/458; 607/122; 606/41
[58] Field of Search ............................ 600/439, 458, 600/461–463, 471, 381; 606/41; 607/116, 101–102, 120, 122, 126–128

[56] References Cited

U.S. PATENT DOCUMENTS

| | | | |
|---|---|---|---|
| 4,565,200 | 1/1986 | Cosman | 128/642 |
| 4,706,681 | 11/1987 | Breyer et al. | 128/786 |
| 4,920,978 | 5/1990 | Colvin | 128/784 |
| 5,385,148 | 1/1995 | Lesh et al. | 600/439 |
| 5,409,000 | 4/1995 | Imran | 128/642 |
| 5,458,597 | 10/1995 | Edwards et al. | 606/41 |
| 5,536,267 | 7/1996 | Edwards et al. | 606/41 |
| 5,569,244 | 10/1996 | Hahnen | 606/46 |
| 5,588,432 | 12/1996 | Crowley | 600/439 |
| 5,740,808 | 4/1998 | Panescu et al. | 600/439 |
| 5,752,518 | 5/1998 | McGee et al. | 600/463 |
| 5,792,140 | 8/1998 | Tu et al. | 606/41 |

*Primary Examiner*—Francis J. Jaworski

[57] ABSTRACT

An RF ablation apparatus has a delivery catheter with distal and proximal ends. A handle is attached to the proximal end of the delivery catheter. The delivery catheter has an electrode deployment means where said electrode deployment means includes a retractable tip section comprising a deployable electrode with portion of one side having a sharp edge. The tip section has a non-deployed state when it is positioned in the delivery catheter. On the other hand, the tip section has a distended deployed state when it is advanced out of the distal end of said delivery catheter. The deployed tip section has a preformed shape while the farther distal deployed electrode defines an ablation target along with portion of the forward side having a sharp edge on said electrode. The forward edge of the deployed electrode has a slightly curvature or an essentially straight shape. Said deployable electrode has ultrasonic imaging capabilities.

14 Claims, 5 Drawing Sheets

ABLATION APPARATUS WITH ULTRASONIC IMAGING CAPABILITIES

FIELD OF THE INVENTION

The present invention generally relates to novel constructions for tissue ablation system. More particularly, this invention relates to ablation apparatus with ultrasonic imaging capabilities and methods for treatment of body tissues, such as tumors by simultaneously encircling the tumor with a sharp edge electrode and applying RF energy for ablation. The apparatus penetrates normal tissue or passes through a natural body opening to reach the target tissue via ultrasonic imaging and delivers therapeutic energy to the target tissue while loosens the target tissue for improved treatment. This ablation apparatus is suitable for reducing the mass of any type of tissue, and is most particularly useful for treating tissue containing tumor cells and the like.

BACKGROUND OF THE INVENTION

Majority of current tumor management approaches are related to surgical means. Surgical treatment of cellular tissues usually exposes both the target and surrounding tissues to substantial trauma and the procedure is costly and time consuming. During a surgical procedure, precise placement of a treatment apparatus is difficult because of the specific location of a target tissue in the body or the proximity of the target tissue to obstructions or easily damaged critical body organs, such as nerves and blood vessels. In the past few years, new products with an emphasis on minimally invasive approaches are being progressively developed to replace the traumatic nature of traditional surgical procedures.

There has been a relatively significant amount of development activity in the field of high energy as a tool for treating tumors. It is known that elevating the temperature of tumors is helpful in the treatment and management of cancerous tissues. The mechanisms of selective cancer cell eradication by high energy doses are not completely understood. However, Edwards et al. in U.S. Pat. No. 5,536,267 hypothesized certain cellular effects of high energy on cancerous tissues. Nevertheless, treatment methods for applying heat to tumors include the use of direct contact radio-frequency (RF) applicators, microwave radiation, inductively coupled RF fields, ultrasound, laser, and a variety of simple thermal conduction techniques.

In the last few years, high frequency currents were used in electrocautery procedures for cutting human tissues, especially when a bloodless incision is desired or when the operating site is not accessible with a normal scalpel but presents an access for a thin instrument through natural body openings such as the esophagus, intestines, uterus, or urethra. Examples include the removal of prostatic adenomas, bladder tumors or intestinal polyps. In such cases, the high frequency current is fed by a surgical probe into the tissue to be cut. The resulting dissipated heat is controlled so that no boiling and vaporization of the cell fluid occurs at this point. The frequency of the current for this use must be above ca. 300 kHz in order to avoid any adverse effect such as nerve and/or muscle responses.

Destruction of cellular tissues in situ has been used in the treatment of many diseases and medical conditions alone or as an adjunct to surgical removal procedures. It is often less traumatic than surgical procedures and may be the only alternative where other procedures are unsafe or unavailable. Ablative treatment apparatus has the advantage of using a destructive energy which is rapidly dissipated and reduced to a non-destructive level by conduction and convection forces of natural body process. Ablative energy may also be controlled by a close-loop temperature sensing and control mechanism.

The same is true for ablation of the tumor itself through the use of RF energy. Different methods have been utilized for the RF ablation of masses such as tumors. Instead of heating the tumors it is ablated through the application of RF energy. This process has been difficult to achieve due to a variety of factors, such as access site, probe location, electrode positioning and energy level. Among them, the most critical factor is the positioning of the RF ablation electrode to effectively ablate all of the mass by controlled delivery and monitoring of RF energy to achieve successful ablation without damage to the surrounding healthy tissue. An ablation apparatus with ultrasonic imaging capabilities meets the positioning requirements.

There have been a number of different treatment methods and apparatus for minimally invasively treating tumors. One such example is an endoscope that produces RF hyperthermia in tumors, as described in U.S. Pat. No. 4,920,978. In U.S. Pat. No. 4,920,978, an endoscope for RF hyperthermia is disclosed. In U.S. Pat. No. 4,565,200, an electrode system is described in which a single entrance tract cannula is used to introduce an electrode into a selected body site. In U.S. Pat. No. 5,458,597, an RF probe with fluid infusion capability is described. Similarly, in U.S. Pat. No. 5,536,267, a multiple electrode ablation apparatus with fluid infusion means is disclosed. For the system with a close-loop temperature control mechanism, the fluid infusion means for the sole purpose of cooling-off the tissues may not be required. Recent clinical studies have indicated that RF energy is rapidly dissipated and reduced to a non-destructive level by conduction and convection forces of natural body process. In all examples, the tissue destruction energy and/or substances have been used to destroy malignant, benign and other types of cells and tissues from a variety of anatomic sites and organs. Tissues treated include isolated carcinoma masses and target tissues in organs such as prostate, glandular and stromal nodules characteristic of benign prostate hyperplasia.

After the exact location of a target tissue is identified, the ablation apparatus may still not easily approach the target site even with assistance of an internal viewing means, such as an endoscope. This viewing situation may turn into a nightmare when an endoscope approach becomes prohibitive or unavailable during procedures. An external ultrasonic imaging capability therefore becomes in need so that ablation is not taking place in an inappropriate location.

In the U.S. Pat. No. 4,794,931, there has been disclosed a catheter apparatus and system which can be utilized for ultrasonic imaging. However, there is no disclosure to how such an apparatus and system can be utilized in conjunction with a tissue ablation apparatus to achieve the desired ultrasonic imaging. In U.S. Pat. No. 5,409,000, an endocardial mapping and ablation system with ultrasonic imaging capabilities is disclosed. However, there is no disclosure to how such a system can be utilized in tissue ablation which is anatomically different from an endocardial ablation.

There is therefore a need for an RF ablation apparatus with ultrasonic imaging capabilities that is useful for treatment and reduction of undesired body tissues by minimally invasive procedures. It would be desirable for such an apparatus to surround the circumferential base of a tumor via ultrasonic imaging and comprising treatment electrodes to define a controlled ablation amount of RF energy by monitoring the temperature and controlling the energy delivered. Additionally, there is a need for an ablation apparatus with a sharp edge electrode to loosen the target tissue for improved ablation treatment. This would provide for the most effective method for reducing the mass of any type of tissue containing tumor cells and the like.

SUMMARY OF THE INVENTION

In general, it is an object of the present invention to provide an improved ablation apparatus with ultrasonic imaging capabilities which can be used in ablating a desired tissue mass, such as a tumor, in a minimally invasive manner. In one embodiment, an RF ablation apparatus has a delivery catheter with distal and proximal ends wherein a semi-flexible flat wire is located within the lumen of said delivery catheter. A handle is attached to the proximal end of the delivery catheter. The flat wire which is semi-flexible as well as semi-rigid is made of a conductive material, such as stainless steel and has a cross-sectional shape and stiffness sufficient to serve as a mechanical support in advancing the ablation apparatus during insertion and RF ablating operations. In a further embodiment, said wire serves as a conducting means for the distal electrode to be connected to an external RF generator for RF energy transmission. The proximal end of said wire is attached to a push-pull mechanism on the handle.

The delivery catheter has an electrode deployment means. The electrode deployment means includes a retractable tip section, which constitutes the distal part of said flat wire, comprising a farther distal deployable electrode having ultrasonic imaging capabilities. Said electrode is consisted of blunt sides except portion of one side having a sharp edge. The sharp edge has a conductive surface for RF energy delivery while the remaining surfaces and edges are non-conductive. The tip section has a non-deployed state when it is positioned in the delivery catheter. This non-deployed state is maintained during an apparatus insertion step into a patient and during withdrawal of the apparatus from a patient.

The tip section has a distended deployed state when it is advanced out of the distal end of said delivery catheter. Deployment of the tip section is accomplished by a pushing action on the push-pull mechanism at the handle. The deployed tip section has a preformed shape so that the tip section would extend outwardly to one side of the delivery catheter when deployed. In the meantime, the distal deployed electrode has a pre-installed torsion spring so that the electrode bends inwardly to the opposite side of the delivery catheter.

The deployed electrode defines an ablation target along with portion of the front side of the electrode having a sharp edge. The front side of the deployed electrode has a slightly circular shape, either concave or convex, to encircle the target tissue. In still another embodiment, a portion of said front side of the deployed electrode has an essentially straight edge. In a further embodiment, the front side of the deployed electrode has sections with plurality of concave or convex curvatures to encircle the target tissue mass.

A conducting wire which is soldered to the proximal end of said flat wire passes through the interior void of the handle and is thereafter soldered to a contact pin of the connector at the proximal end of the handle. From there, the conducting wire is connected to an external RF generator for ablation operations. The ablation apparatus may further comprise a steering mechanism at the handle for controlling the deflection of the distal section of the delivery catheter. Usually a rotating ring or a secondary push-pull plunger on the handle is employed as integral part of the steering mechanism. One end of the steering wire is attached at certain point of the tip section of said flat wire while the other end is attached to the steering mechanism at the handle. The steering mechanism on a steerable catheter or device is well-known to those who are skilled in the art. In an additional embodiment, the ablation apparatus further comprises a temperature sensing and close-loop temperature control mechanism for the electrode having a temperature sensor at the tissue contact site. The location of the temperature sensor is preferably in the proximity of the sharp edge of the electrode. The ultrasonic viewing markers are also located in the proximity of the sharp edge of said electrode.

The delivery catheter having a tip section under a non-deployed state is inserted into the body through a small surgery hole or through a natural body opening such as esophagus, intestines, uterus, or urethra. After the catheter approaches the target tissue mass to be treated, the tip section is deployed by being pushed out of the delivery catheter from a push-pull mechanism at the handle. By using an ultrasonic viewing setup, the markers on the electrode can be employed to locate said electrode. Once positioned, the sharp edge of the electrode encircles the circumferential base of the tissue mass. By simultaneously or alternately gradually pushing forward the catheter against the tissue mass and applying RF energy, the target tissue mass is loosened, reduced and treated as a result of a combination of the RF energy and mechanical cutting force.

In a further embodiment, the deployable electrode having a sharp edge at its front side loosens the target tissue while delivers therapeutic energy for improved treatment. Said electrode is suitable for reducing the mass of any type of tissue, particularly effective for treating tumor tissue, such as the removal of prostatic adenomas, bladder tumors, uterus tumors, urethra's tumors, intestinal polyps and the like.

Another object of the invention is to provide an apparatus and methods in which it is possible to view the area to be ablated prior to ablation to ensure that ablation is being carried out in an appropriate location. The electrode having a sharp edge is encoded with plurality of markers which are visible to ultrasonic energy. The markers have been provided in the form of encapsulated air bubbles. In another embodiment, probes with ultrasonic signal capability are located adjacent to the sharp edge of said electrode. The ultrasonic signals are directed outwardly and received inwardly relative to the front side of the electrode to permit rapid and substantially continuous viewing of the target tissue. The method and apparatus of the present invention have several significant advantages over known ablation apparatus or ablation techniques. In particular, the electrode of an ablation apparatus of this invention results in a more accurate means for ascertaining the area to be ablated and a more effective means for reducing the mass of any type of tissue containing tumor cells and the like.

BRIEF DESCRIPTION OF THE DRAWINGS

Additional objects and features of the present invention will become more apparent and the invention itself will be best understood from the following Detailed Description of the Preferred Embodiments, when read with reference to the accompanying drawings.

DETAILED DESCRIPTION OF THE PREFERRED EMBODIMENTS

Figure 1:
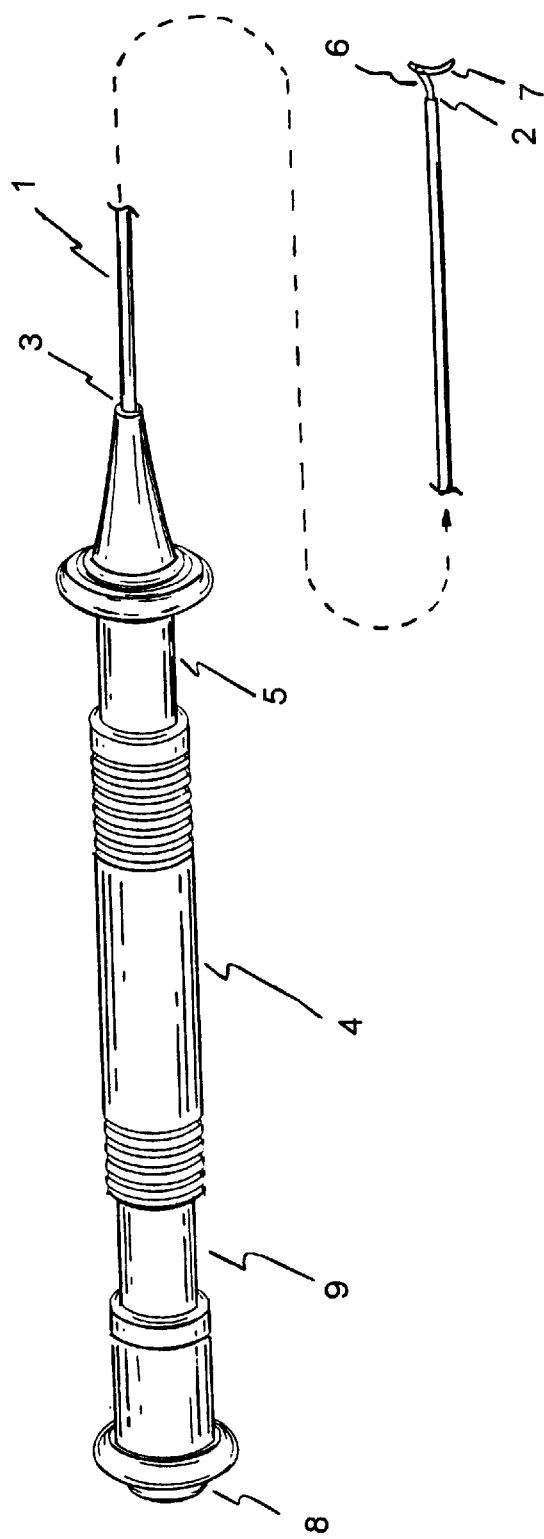
FIG. 1 is a prospective view of the ablation apparatus having an electrode deployment means comprising a retractable tip section and an electrode with ultrasonic imaging capabilities in accordance with the principles of the present invention.

An ablation apparatus constructed in accordance with the principles of the present invention comprises: a delivery catheter with distal and proximal ends wherein a semi-flexible flat wire is located within the lumen of said delivery catheter. FIG. 1 shows a prospective view of the ablation apparatus having a delivery catheter 1 with a distal end 2 and a proximal end 3. A handle 4 is attached to the proximal end 3 of said catheter 1. The proximal end of said flat wire is attached on a push-pull mechanism 5 on the handle 4. The distal end of said flat wire comprises an outwardly extended tip section 6 and a farther distal electrode 7. The semi-flexible flat wire serves as a conducting means for the electrode to be connected to an external RF generator. Said flat wire with sufficient stiffness also serves as a mechanical support in advancing the ablation apparatus during insertion operation and during RF ablating operation.

An insulated conducting wire which is soldered to the proximal end of said semi-flexible flat wire passes through the interior void of the handle 4 and is thereafter soldered to a contact pin of the connector 8 at the proximal end of said handle. From there, the conducting wire is connected to an external RF generator for RF energy transmission. In a further embodiment, the ablation apparatus may further comprise a steering mechanism 9 at the handle 4 for controlling the deflection of the distal section of the delivery catheter 1. One end of the steering wire is attached at certain point of the tip section 6 of said flat wire while the other end is attached to the steering mechanism 9 at the handle 4. The steering mechanism on a steerable catheter is well-known to those who are skilled in the art.

In an additional embodiment, the ablation apparatus further comprises a temperature sensing and close-loop temperature control mechanism for the electrode having a temperature sensor at the tissue contact site of said electrode 7. Temperature sensing wires along with a thermocouple or thermistor means is provided to transmit the temperature data from the tissue contact site to an external temperature measuring and control apparatus (not shown). An algorithm is installed in the ablation system so that a close-loop temperature control is effective and the temperature data is relayed to an RF generator for controlled energy delivery.

Figure 2:
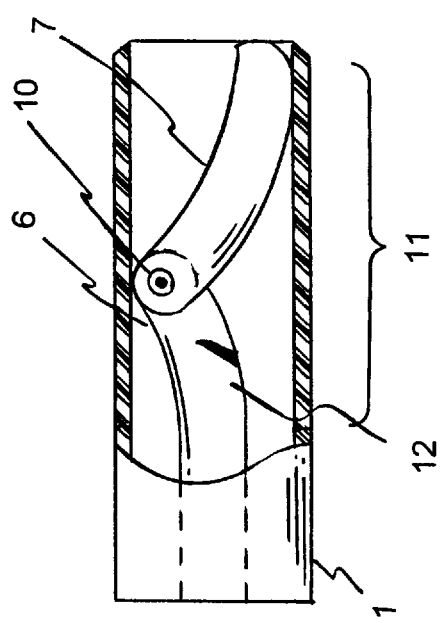
FIG. 2 is a close-up view of the retractable tip section at non-deployed state.

FIG. 2 is a close-up view of the retractable tip section at non-deployed state. The semi-flexible flat wire 12, having a retractable tip section 6, is located within the lumen of the delivery catheter 1. A deployable electrode 7 is located at the farther distal end of said tip section 6. The non-deployed state is maintained during apparatus insertion into a patient and apparatus withdrawal from a patient. Under non-deployed state, the tip section 6 which has a preformed shape tends to tilt to one side of the delivery catheter 1 while the electrode 7 which has a pre-installed torsion spring tends to tilt to the opposite side of said delivery catheter 1. The torsion spring (not shown) is located at the joint 10 between the tip section of said flat wire and the deployable electrode. Said torsion spring is positioned in a way that moderate spring force pushes the electrode backwardly when deployed.

In another embodiment, the distal section 11 of said delivery catheter 1 comprises a reinforced shaft to maintain essentially its circular cross-section shape even under the impact of the preformed tip section 6 and/or pre-installed spring-loaded electrode 7. Reinforcement of the distal shaft of said catheter can be accomplished either by a braided tubing or a tubing with higher hardness welded to said delivery catheter 1.

Figure 3:
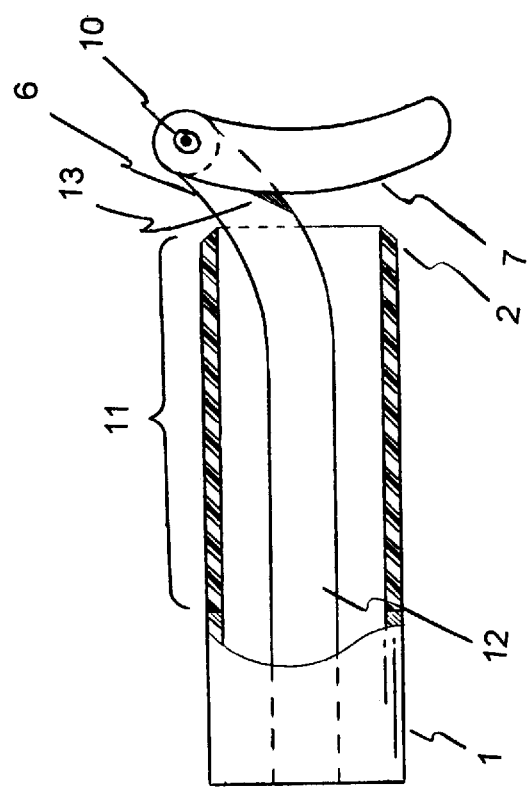
FIG. 3 is a close-up view of the retractable tip section at fully deployed state.

FIG. 3 shows a close-up view of said retractable tip section at fully deployed state. The tip section 6 has a distended deployed state when it is advanced out of the distal end 2 of said delivery catheter 1. Deployment of the tip section is accomplished by a pushing action on a push-pull mechanism 5 at the handle 4. Because of its preformed shape, the distal tip section 6 extends outwardly to one side of said catheter when deployed. In the meantime, the deployed electrode 7 bends inwardly to the opposite side of said catheter 1 because of its pre-installed torsion spring. The spring-loaded electrode can only bend backwardly to certain position when it is fully deployed because of a lower stopper 13 on the tip section 6.

Figure 4:
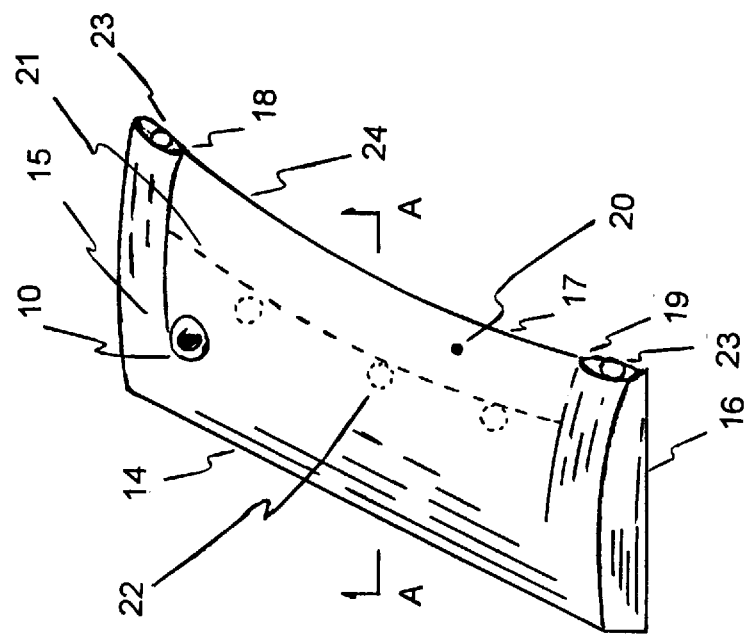
FIG. 4 is a prospective view of the electrode having a sharp edge on its front side of FIG. 3.

FIG. 4 is a prospective view of the electrode having a sharp edge on its front side. The electrode comprises a front side 24, a backward side 14, a top side 15 and a bottom side 16 (not shown). The front side has a sharp edge 17 which is located between the points 18 and 19. The location of a temperature sensor is preferably in the proximity of the sharp edge of said electrode 7.

The sharp edge may be a straight edge, a curved edge or an edge with plurality of curvatures. The surface of said electrode is coated with an insulating material except the front body of the sharp edge, where a temperature sensor 20 is located. In a particular embodiment, the front body of said sharp edge having conducting surface may range from a fraction of millimeter to several millimeters. The front body of said electrode 7 is defined as the section bordered by the sharp edge 17, an imaginary line 21 and the boundary lines between the sharp edge and the blunt edge, starting from points 18 and 19. In another embodiment, the deployable electrode other than said front body is made of a non-conductive plastic material.

The front side 24 outside of the points 18 and 19 is a blunt edge where ultrasonic probes 23 are located. The ultrasonic probes are connected by flexible wires (not shown) through the interior voids of the ablation apparatus to the connector 8 at the proximal end of the handle 4 so that the ultrasonic signals are directed outwardly and received inwardly relative to the probes 23 which advance along with the front side 24 of said electrode 7. In order to enhance the ablation positioning of said ablation apparatus, the electrode is encoded with markers 22 which are visible to ultrasonic energy. Such markers 22 are provided in the form of encapsulated air bubbles. Several markers 22 are placed in the front body right behind the imaginary line 21 in a way so that the exact location of the sharp edge 17 is visible to an external ultrasonic energy. By way of example, the bubble in a marker can be formed by introducing air by a syringe (not shown) penetrating the wall of the plastic front body of said electrode and thereafter is sealed by epoxy.

Figure 5:
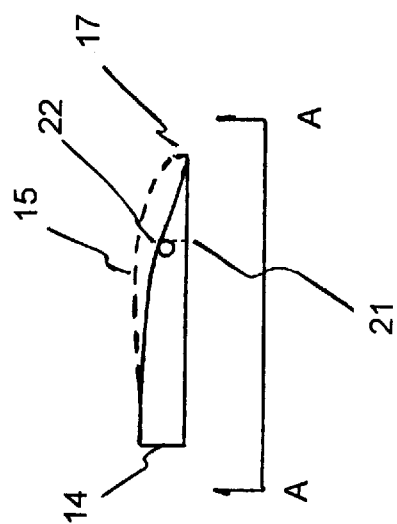
FIG. 5 is a cross-sectional view of the electrode with ultrasonic imaging capabilities of FIG. 4.

As shown in FIG. 5, the sharp edge 17 is at the front side 24 of said electrode 7 while the temperature sensor 20 is in the proximity of the sharp edge. The front body of the front side which ranges from the sharp edge 17 to the imaginary line 21, including the temperature sensor 20, has a conducting surface for RF energy delivery.

From the foregoing, it should now be appreciated that an improved ablation device comprising a sharp edge electrode with ultrasonic imaging capabilities has been disclosed for tissue ablation procedures. While the invention has been described with reference to a specific embodiment, the description is illustrative of the invention and is not to be construed as limiting the invention. Various modifications and applications may occur to those skilled in the art without departing from the true spirit and scope of the invention as described by the appended claims.

What is claimed is:

1. An ablation apparatus comprising:
   (a) a delivery catheter with a distal section, a distal end, a proximal end, and a lumen extending therebetween, wherein a wire having a distal end and a proximal end is located within the lumen of the delivery catheter;
   (b) a handle attached to the proximal end of said delivery catheter, wherein a push-pull mechanism is located within the handle, and wherein the proximal end of the wire is attached to the push-pull mechanism;
   (c) an electrode deployment means positioned at the proximal end of the wire, wherein the wire comprises a retractable tip section; the catheter, handle, wire, and deployment means being adapted to cooperate to house non-deploy and deploy the tip section;
   (d) an electrode mounted on the retractable tip section, wherein the electrode has a front side adapted to contact the tissue when the retractable tip section is deployed; and
   (e) ultrasonically visible markers mounted on the distal catheter tip on the electrode.

2. The ablation apparatus as in claim 1, further comprising a preformed shape for the retractable tip section, wherein the tip section extends outwardly to one side of the delivery catheter when it is deployed.

3. The ablation apparatus as in claim 2, further comprising a torsion spring for the at least one electrode mounted on the retractable tip section, wherein the electrode bends inwardly to the opposite side of the delivery catheter with respect to the tip section.

4. The ablation apparatus of claim 3, wherein a portion of the front side of the electrode has an essentially straight edge.

5. The ablation apparatus as in claim 3, further comprising a steering mechanism at the handle for controlling the deflection of the distal section of said delivery catheter.

6. The ablation apparatus of claim 5, wherein the front side of the electrode has a slightly circular shape.

7. The ablation apparatus of claim 5, wherein the front side of the electrode has sections with plurality of curvatures.

8. The ablation apparatus as in claim 5, further comprising a temperature sensor mounted on the electrode and a closed-loop temperature controller, wherein the temperature sensor provides sensing signals for the closed-loop controller for the ablation apparatus.

9. The ablation apparatus of claim 3, wherein the electrode is consisted of blunt sides except a portion of the front side has a sharp edge wherein said sharp edge comprises a conductive surface adapted for RF energy delivery.

10. The ablation apparatus as in claim 3, further comprising ultrasonic probes on the front side of the electrode having ultrasonic signals being directed outwardly and received inwardly relative to the probes which are adapted to advance along with the front side of said electrode.

11. The ablation apparatus of claim 5, wherein the front side of the electrode has a sharp edge.

12. A method for operating an ablation apparatus system inside the body of a patient for ablating a target tissue, the ablation apparatus system comprising a delivery catheter with a distal section, a distal end, a proximal end, and a lumen extending therebetween, wherein a wire having a distal end and a proximal end is located within the lumen of the delivery catheter; a handle attached to the proximal end of said delivery catheter, wherein a push-pull mechanism is located within the handle, and wherein the proximal end of the wire is attached to the push-pull mechanism; an electrode deployment means positioned at the proximal end of the wire, wherein the wire comprises a retractable tip section; the catheter, handle, wire, and deployment means being adapted to cooperate to house non-deploy and deploy the tip section; an electrode mounted on the retractable tip section, wherein the electrode has a front side adapted to contact the tissue when the retractable tip section is deployed; ultrasonically visible markers mounted on the distal catheter tip on the electrode, and an external RF generator, wherein RF is applied by the catheter electrode for ablation purposes;

the method comprising:
   (a) introducing the delivery catheter having a retractable tip section under a non-deployed state into the body through a small surgery hole or through the natural body openings;
   (b) once approaching the target tissue, deploying the tip section by operating the push-pull mechanism at the handle;
   (c) moving the electrode to the proximity of the target tissue guided by the ultrasonically visible markers;
   (d) once positioned at the target tissue, encircling the target tissue; and
   (e) by a simultaneous or alternate mode, gradually pushing forward the delivery catheter against the target tissue and applying RF by the catheter electrode to the tissue.

13. The method for operating an ablation apparatus system inside the body of a patient for ablating a target tissue as in claim 12, further comprising treating body tissue selecting from removal of prostatic adenomas, bladder tumors, uterus tumors, urethra tumors, and intestinal polyps by loosening the tissue and applying RF energy in a simultaneous mode, alternate mode, or a combination thereof.

14. An ablation apparatus comprising:
   (a) a delivery catheter with a distal section, a distal end, a proximal end, and a lumen extending therebetween, wherein a wire having a distal end and a proximal end is located within the lumen of the delivery catheter;
   (b) a handle attached to the proximal end of said delivery catheter, wherein a push-pull mechanism is located within the handle, and wherein the proximal end of the wire is attached to the push-pull mechanism;
   (c) an electrode deployment means positioned at the proximal end of the wire, wherein the wire comprises a retractable tip section; the catheter, handle, wire, and deployment means being adapted to cooperate to house non-deploy and deploy the tip section;
   (d) an electrode mounted on the retractable tip section, wherein the electrode has a front side adapted to contact the tissue when the retractable tip section is deployed, and wherein the electrode is consisted of blunt sides except a portion of the front side having a sharp edge to loosen the target tissue for improved ablation treatment with RF energy delivery; and
   (e) ultrasonically visible markers mounted on the distal catheter tip on the electrode.

* * * * *